(12) United States Patent
Sangha

(10) Patent No.: US 7,587,793 B2  
(45) Date of Patent: Sep. 15, 2009

(54) EVIDENCE COLLECTION HOLDER AND STORAGE METHOD

(75) Inventor: Jangbir S. Sangha, Overland Park, KS (US)

(73) Assignee: Bode Technology Group, Inc., Springfield, VA (US)

( * ) Notice: Subject to any disclaimer, the term of this patent is extended or adjusted under 35 U.S.C. 154(b) by 0 days.

(21) Appl. No.: 11/042,527

(22) Filed: Jan. 25, 2005

(65) Prior Publication Data

US 2005/0147537 A1     Jul. 7, 2005

Related U.S. Application Data

(63) Continuation-in-part of application No. 10/020,257, filed on Dec. 14, 2001, now abandoned.

(60) Provisional application No. 60/567,081, filed on Apr. 30, 2004, provisional application No. 60/617,100, filed on Oct. 7, 2004.

(51) Int. Cl.
*G01N 33/48*     (2006.01)
*G01N 33/49*     (2006.01)
*G01N 33/22*     (2006.01)
*G01N 33/50*     (2006.01)

(52) U.S. Cl. .............................. 422/58; 422/56; 422/61; 422/99; 422/102; 422/104; 73/864.91

(58) Field of Classification Search ................... 422/56, 422/58, 61, 99, 102, 104; 73/864.91
See application file for complete search history.

(56) References Cited

U.S. PATENT DOCUMENTS

| 5,409,832 | A | * | 4/1995 | Pocock | 435/288.3 |
| 5,597,532 | A | * | 1/1997 | Connolly | 422/58 |
| 5,612,870 | A | * | 3/1997 | Welner | 705/3 |
| 2002/0061597 | A1 | * | 5/2002 | Herpst | 436/164 |

* cited by examiner

*Primary Examiner*—Jill Warden
*Assistant Examiner*—Paul S Hyun
(74) *Attorney, Agent, or Firm*—Polsinelli Shughart, P.C.; Richard P. Stitt

(57) ABSTRACT

A device and method of securing the original biological specimen collection absorbent within a holder to permit use of the absorbent within automatic specimen analysis devices and to permit continuance of a chain of custody is provided.

12 Claims, 17 Drawing Sheets

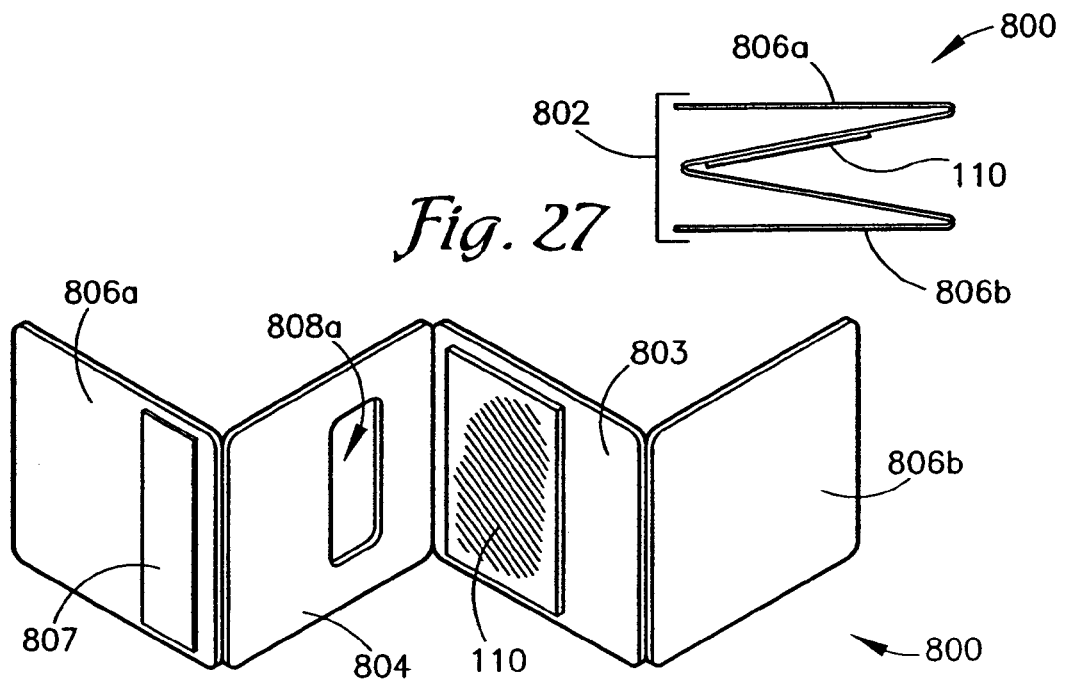
Fig. 27
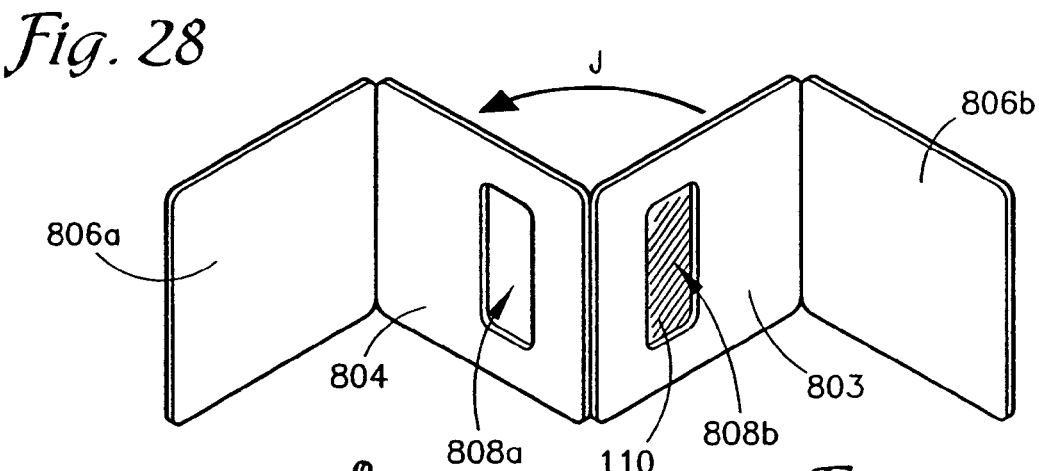
Fig. 28
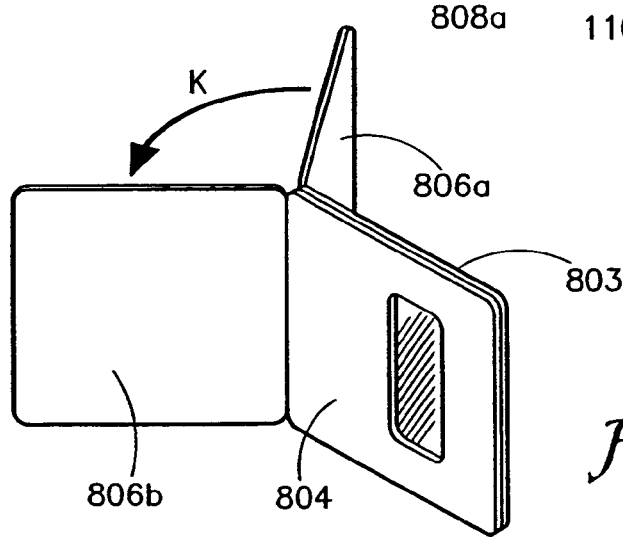
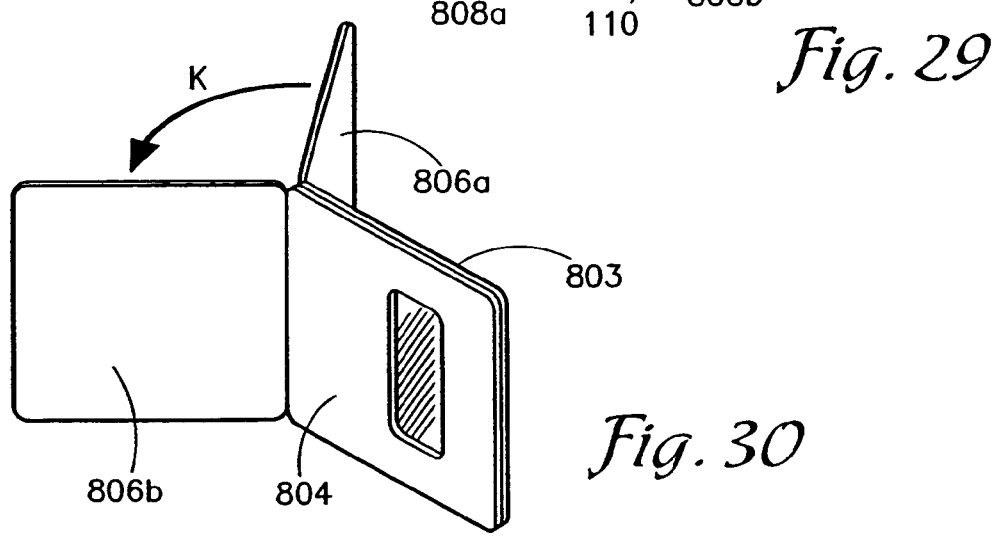
Fig. 29
Fig. 30

EVIDENCE COLLECTION HOLDER AND STORAGE METHOD

CONTINUATION DATA

This application is a continuation-in-part application of application Ser. No. 10/020,257 filed Dec. 14, 2001, now abandoned. The specification of U.S. Pat. No. 6,440,087 is incorporated herein by reference. This application further claims priority to provisional patent application Ser. No. 60/567,081 filed Apr. 30, 2004, and provisional patent application Ser. No. 60/617,100 filed Oct. 7, 2004.

FIELD OF THE INVENTION

The field of the present invention is devices for collecting biological samples. In particular, the several embodiments of the present invention provide a device having an absorbent for collection of oral fluids or blood specimens or cells thereon. Several embodiments of the specimen collection devices provide for recordation of identifying information and for division of the sample into separate identifiable portions to permit use of the specimen as law enforcement evidence. Generally, the embodiments of the invention further provide a holder for containing and/or securing the original specimen collection material or paper or absorbent that was used in the actual collection of the biological specimen or sample. The holder permits the original collection paper or absorbent to be processed by automated analysis equipment by securing the collection paper or absorbent in a holder that is structured to permit extraction of a test sample while maintaining the evidentiary requirements necessary for a proper chain of custody.

The invention allows for collecting saliva from the mouth or blood samples from a suspect or mammal or DNA samples while later permitting extraction of portions of the sample collection absorbent for testing while maintaining the chain of evidence and identification of the specimen of saliva or blood.

BACKGROUND OF THE INVENTION

Increasingly in law enforcement it is necessary to collect biological samples as evidence of a crime or for use as identifying information of a particular human as is the case of DNA collection from suspects. In the collection of biological specimens, it is necessary to associate information about the subject with the specimen at the time of collection as there is no manner for identifying a biological specimen by simple inspection. Therefore, a useful form of evidence collection device for use with biological specimens will contain, at least, a suspect information portion for recording subject information data thereon.

The use of biological specimens as evidence further requires that the biological specimen be securely associated with the identifying information so as to assure that after collection of the specimen, the collection paper or absorbent cannot be intentionally or inadvertently switched to a different collection paper. At a minimum, a proper evidence collection device or holder should easily and clearly show that tampering was attempted either by damage to delicate indicia on the device or by overt damage to a strongly secured device. It is further beneficial if the evidence collection device can accommodate additional forms of evidence such as the application and storage of finger prints on the evidence holder.

A particular issue in the collection of the biological sample is that the sample collection is often taken from a living, uncooperative person. Often the sample is to be taken from the mouth of the suspect where a saliva or DNA specimen is needed. In this instance, the collection absorbent used with the attached to a handle or a stick. Once the specimen is on the absorbent, the handle is no longer needed, a present complicating factor in specimen storage and analysis due to the extra bulk and size.

The foregoing issues relate, generally, to a process referred to as evidence "chain of custody." "Chain of custody" encompasses the procedures and documentation used to maintain and demonstrate the chronological history of the evidence. Documentation should include, for example, name or initials of the individual collecting the evidence, each person or entity subsequently having custody of it, dates the items were collected or transferred, agency and case number, victim's or suspect's name, and a brief description of the item. In biological samples, the principles of evidence or sample identification involved in maintaining proper "chain of custody" are especially critical as a fluid or cellular biological sample, once collected onto an absorbent presents no distinguishing characteristics. This lack of visual characteristics foils any attempt to properly identify such a biological fluid or cellular sample once it has become separated from its identifying information.

Another problem or issue presented in the analysis of biological specimens is the need to extract or transfer the collected sample from the original collection absorbent and onto an alternate medium to permit analysis or testing of the specimen using the analysis equipment that is available in the selected laboratory. Often it is necessary to separate the collection absorbent from its originally obtained identifying information that is directly associated with the original collection absorbent. This separation of specimen from identifying information can lead to mistakes in associating the specimen with the correct subject or suspect or can lead to the "chain of custody" being open to question in court and a failure of proof of a crime. Sample misidentification is a major source of error both in laboratory analysis and in substantiating criminal evidence.

An additional issue associated with the collection of the biological sample is the need to test or analyze the sample for comparison purposes with other specimens. The sample analysis must be conducted using preexisting instrumentation which is not amenable to maintaining the "chain of custody" of a biological specimen absorbent. For example, in automatic sample testing devices originally designed for the insurance testing industry, the standards of assuring the association of a specimen with its identifying information is not as rigorous as is required for evidence "chain of custody."

Therefore, it would be a benefit if a biological sample holder and storage device were available which securely associated the biological specimen absorbent with the subject identifying information and which permitted removal of any handle portion attached to the collection absorbent and which was tamper proof or tamper evident and which provided ease of use for the collection law enforcement officer while in the field.

DESCRIPTION OF THE DRAWINGS

Preferred embodiments of the invention, illustrative of the best modes in which the applicant has contemplated applying the principles, are set forth in the following description and are shown in the drawings and are particularly and distinctly pointed out and set forth in the appended claims.

FIG. 27 is a side elevation view of yet another embodiment of a collection paper holder and sampling device and showing absorbent 110 mounted on one side of the card;

FIG. 28 shows the embodiment of FIG. 27 partially expanded to reveal absorbent 110 mounted thereon and window 808a aligned with absorbent 110;

FIG. 29 shows the embodiment of FIG. 27 as it is assembled together by movement of side 803 against 804 along arrow J;

FIG. 30 shows side 803 in contact with side 804 and side 806a being moved toward side 806b along arrow K;

DESCRIPTION OF THE PREFERRED EMBODIMENTS

The purpose of the various inventive sample holders or specimen/sample carriage devices shown in the present application is to meet collection requirements which allow blood specimen collection or body fluid collection or DNA collection to qualify for secure evidence handling and for chain of custody proof requirements in law enforcement. In particular, in an optimal situation, it is desirable that the sample holder used for adapting the sample or specimen collection device to an automated sampling system incorporate the original specimen collection absorbent and avoid the need for any transfer of the specimen onto a second absorbent or require the transfer of a bar code or other identifying material from the collection absorbent or DNA collector or sampling device onto the sample device holder. It is far more desirable and preferable that the original specimen collection absorbent and the same bar code that is attached to the original sample or specimen collection absorbent or device be inserted into the sample holder and be viewable from within the sample or specimen holder. It also is important that the absorbent or sampling paper surface, while held within the holder, be exposed so that small portions or circles can be punched from the paper for delivery into testing vials for making the DNA determination.

It is also another important feature that the sample holder have a locking feature so that once the sample collection device and/or absorbent is fixed within the holder, it is locked into the holder, and the holder cannot be tampered with or opened without the damage being evident. It is another benefit if the holder for such automated sampling avoids a secondary transfer of the original collection absorbent 110 (FIG. 10) of collector or collection device 106 (FIG. 10) or any destruction of the original sample device 106 and/or collection absorbent 110 and maintains the original collection absorbent 110 (FIG. 10) attached or within its handle and bearing its original bar code marking and other identifying markings. This is desirable to eliminate any mix up between samples due to transfer of the original identifiers associated with the sample during the moment of sample collection onto sample holders used during analysis of the sample. It is another important benefit that separation of the sample from the handle or transfer of bar codes or other identity material be avoided. This is desirable to avoid complication of the chain of custody and to make an unambiguous association between the device that received the subject's blood specimen or went into the subject's mouth to collect the sample and the sample that appears in the laboratory for analysis.

Figure 1:
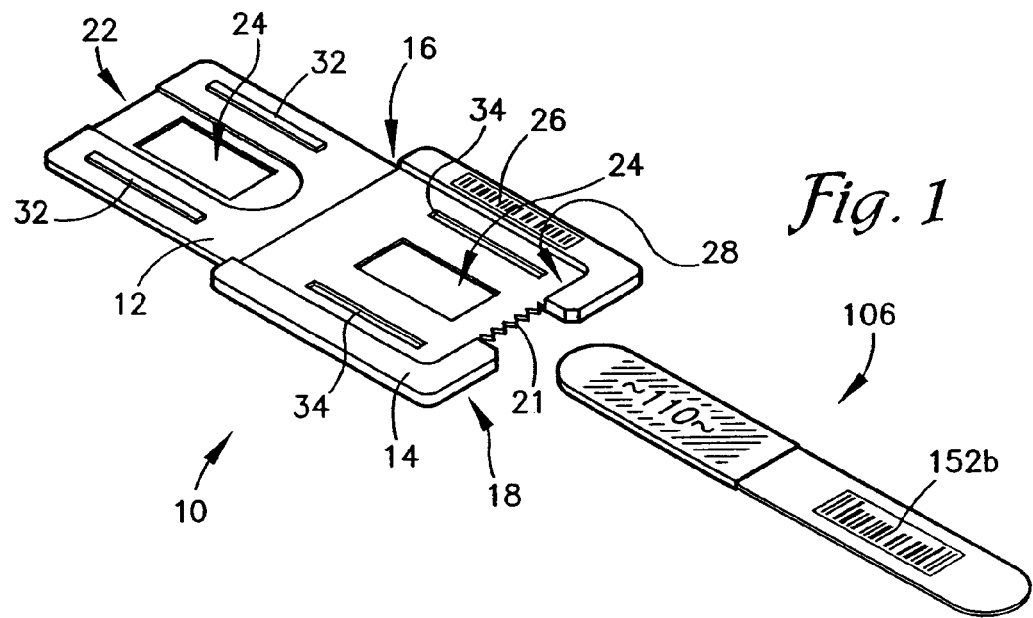
FIG. 1 is a top and front perspective view of a hinged specimen holder.
Figure 2:
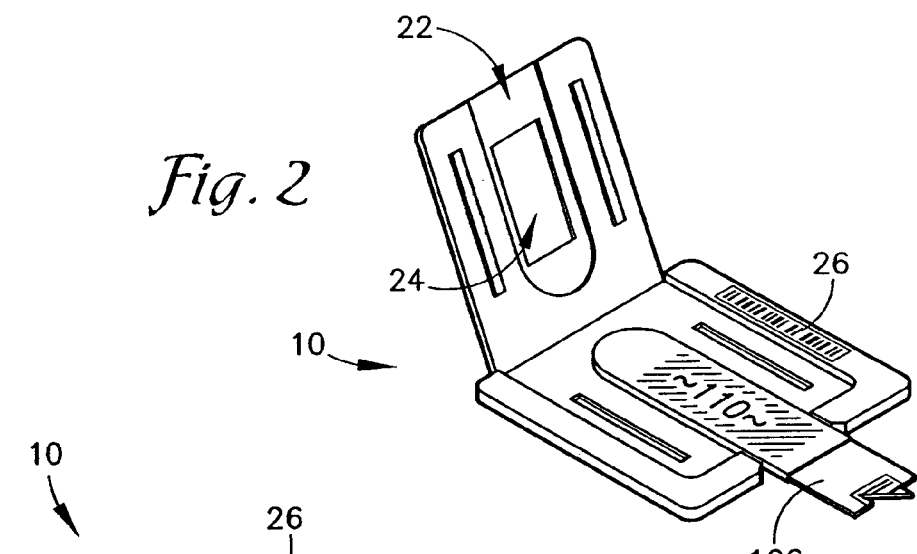
FIG. 2 is a top and front perspective view of the device of FIG. 1 having a collection absorbent inserted therein.
Figure 3:
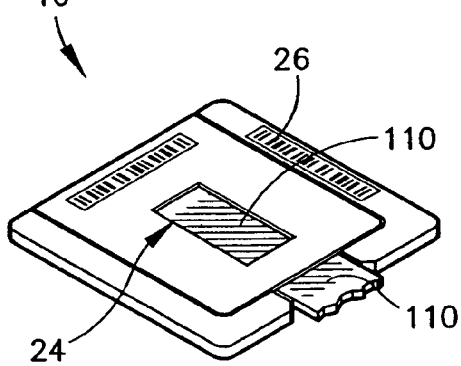
FIG. 3 shows the device of FIGS. 1 and 2 with the hinged lid in closed position to capture the absorbent 110 therein and with the absorbent handle torn away from the absorbent 110 by the assistance of cutter 21.

Referring now to FIGS. 1-3, a sample carriage device embodiment 10 is shown which allows the paper absorbent 110 of the specimen/sample collector 106 to be inserted into the carriage device 10 and the paper absorbent 110 captured within the carriage device and the paper separated from the collector handle 114 (FIG. 10) by serrated edges 21 on device 10.

Referring to FIG. 1, embodiment 10 is comprised of an upper portion 12 which is connected to a bottom portion 14 by the use of a hinge means or staple connection or fold along back edge 16 to permit top portion 12 to be separable from bottom portion 14 along front edge 18. Front edge 18 includes cutter portion 21 having teeth-like edges or serrations in front edge 18 the purpose of which shall be described hereinafter.

Figure 6:
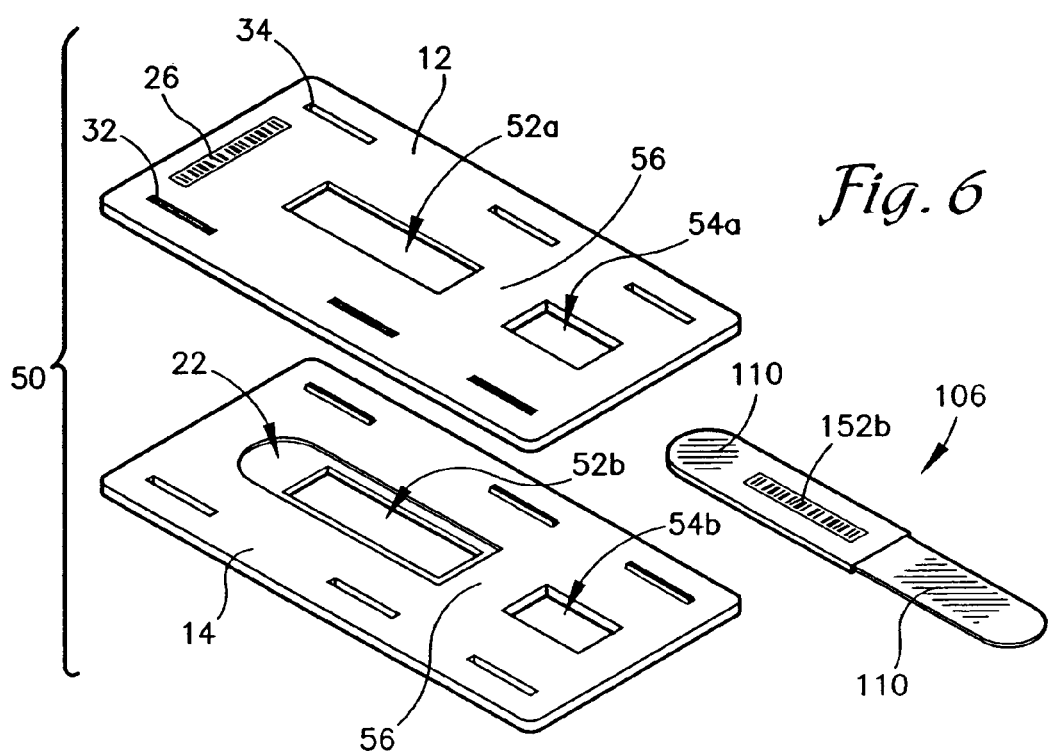
FIG. 6 is an exploded view of yet another embodiment of the specimen collection holder showing the two piece collection holder with the absorbent and handle aligned for insertion and capture therein.
Figure 7:
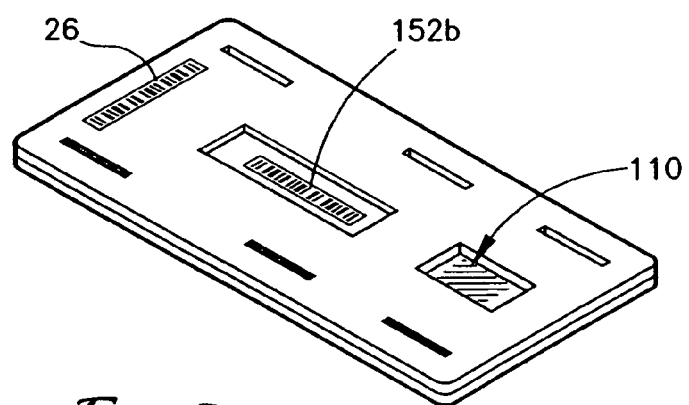
FIG. 7 shows the embodiment of FIG. 6 in assembled fashion with the collection absorbent and handle captured between the two pieces of the holder of the embodiment.
Figure 8:
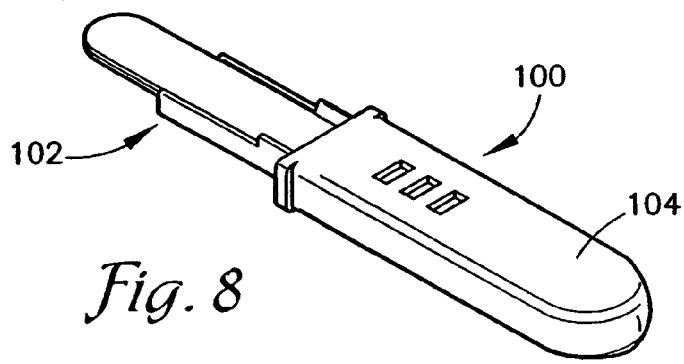
FIG. 8 is a top and side perspective view of an embodiment of a biological specimen collection device with the cover in place over the end of the device.
Figure 9:
FIG. 9 is a top and side perspective view of the collection device of FIG. 8 with the cover removed.
Figure 10:
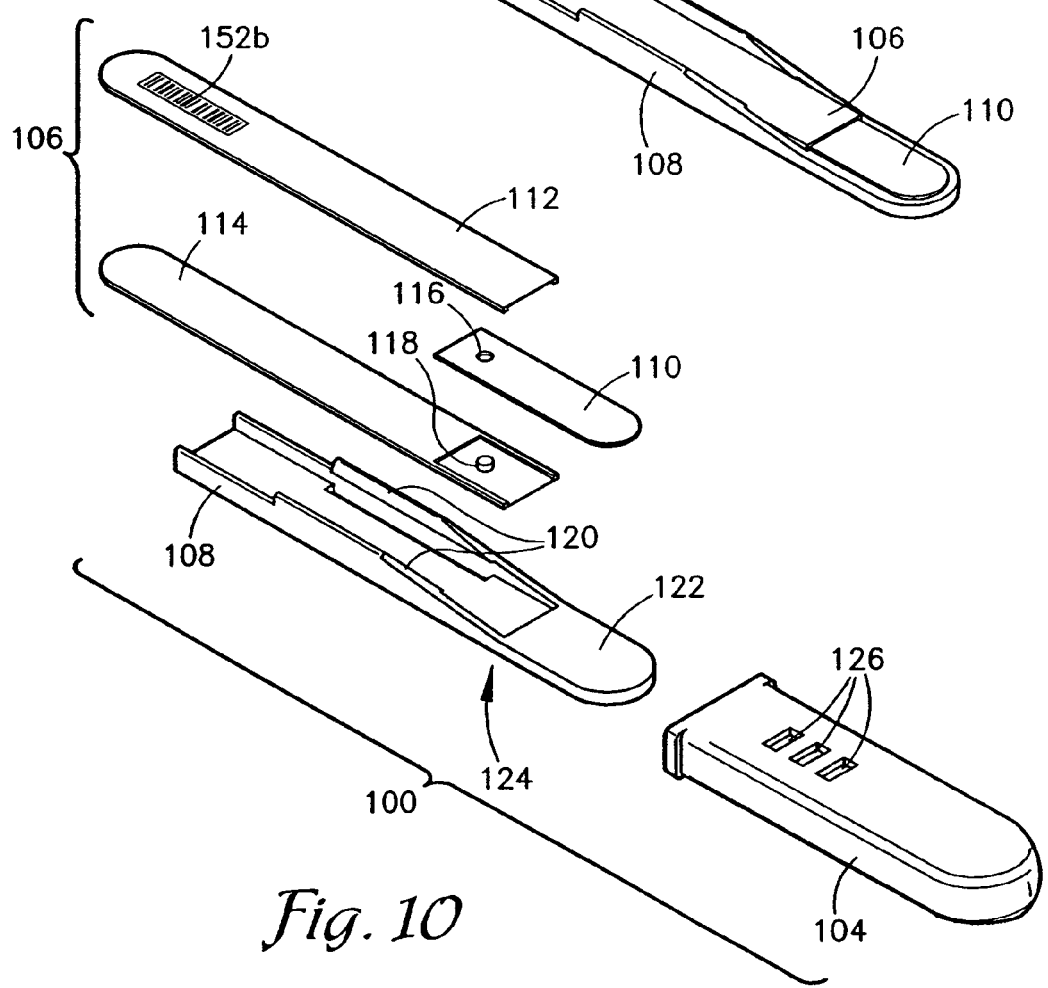
FIG. 10 is an exploded view of the collection device of FIG. 9.

In operation, a specimen or sample collector 106 such as the one shown in FIGS. 8-10 can be used with any of the embodiments of FIGS. 1-7. Other configurations or shapes of absorbents 110 may be used if the registration track or groove 22 of the sample carriage 10 is reconfigured to accept the alternate absorbent shape. The sample carriage 10 shown in FIGS. 1-3 may be operated by removing the handle portion 106 from holder 108 (FIG. 10) and inserting collection absorbent or paper 110, having a specimen or sample thereon, into device 10 such that absorbent or paper 110 is visible within viewing or sample collection area or window 24.

Figure 4:
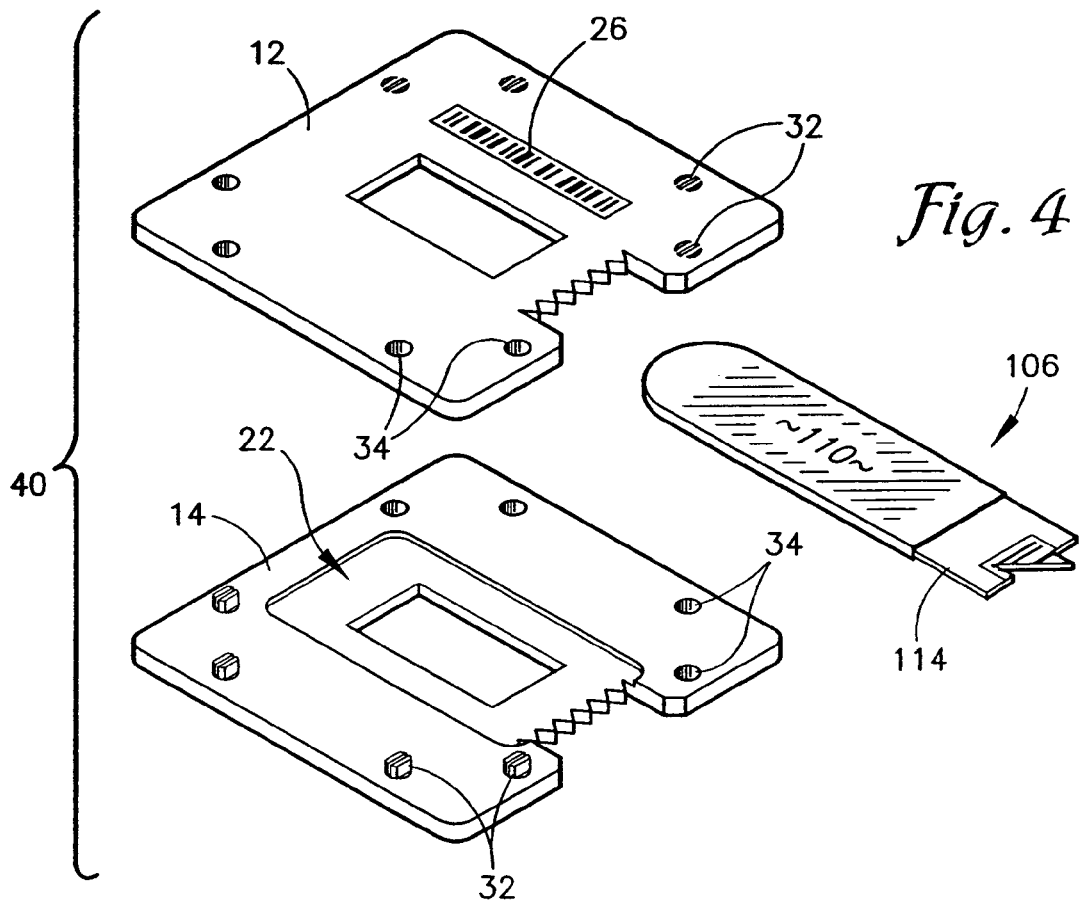
FIG. 4 is an exploded view of an alternate embodiment of the specimen holder showing a two-piece specimen holder with the absorbent aligned for insertion therebetween.
Figure 5:
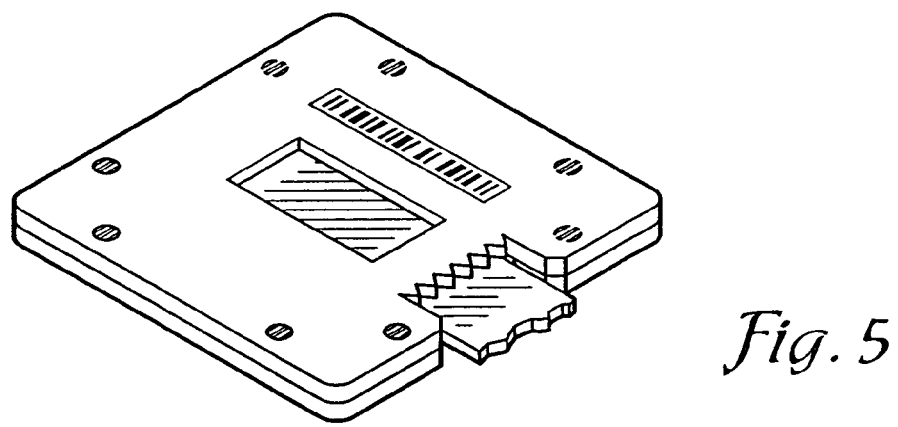
FIG. 5 shows the embodiment of FIG. 4 in assembled relationship with the absorbent captured therein and the handle broken off.

Once the collection paper 110 is positioned so as to be captured within the registration track or groove 22 of holder 10, top portion 12 is pressed against bottom portion 14 to secure absorbent 110 therebetween. Top portion 12 and bottom portion 14 are then held together by a securing means. In device 10 top portion 12 and bottom portion 14 are held together by a frictional fit between top portion 12 and bottom portion 14 as top portion 12 fits into a recessed area 28 of bottom portion 14. Alternatively, or additionally, the securing means may be a post 32 insertable into a detent 34 to lock together top portion 12 and bottom portion 14 as is shown in FIGS. 4-5 for embodiment 30 (FIG. 4). Alternative securing means will be apparent to those skilled in the art, means such as glue or tape or a staple or adhesive strip or a peel and stick or release liner or any convenient means of securing the two surfaces together to hold collection absorbent paper 110 within top portion 12 and bottom portion 14 also may be used. When absorbent paper 110 is secured within the holder 10, serration or cutter 21 may be used to separate the paper 110 from handle portion 106 by using the cutter 21 to separate handle 106 from absorbent 110. This then will present sample absorbent paper 110 locked into the device 10 as is shown in FIG. 3 wherein absorbent sample paper 110 is shown by the cross hatch marks within the window 24 and with the paper now bearing reference numeral 110 to indicate that it is the absorbent sample paper 110 taken from the holder 106.

Once sample paper 110 is fixed within the holder 10, the paper may then be loaded into an automated sampling device such as an automated sample punching machine such as a BSD-1000 manufactured in Australia. The automated sampling device will read bar code 26 on top surface 12 of device 10. A typical automated sampling device will then punch samples from collection paper 110 as it is held within window 24 of holder 10. It will be appreciated that bar code 26 is bar code 152b shown on collection device 106 in FIG. 10 and which has been transferred to the holder 10 during the process of capturing collection absorbent paper 110 within holder 10. Alternatively, a duplicate version of bar code 152b may be produced and placed on device 10 to serve as bar code 26.

Referring now to FIGS. 4 and 5, another embodiment, device 40, is shown which is similar in construction to device 10 of FIGS. 1-3. In describing device 40 the same reference numbers will be used in describing structures that are similar to structures found in device 10. Device or sample holder 40 is comprised of a top or upper portion 12 which is separate from bottom portion 14. As upper or top portion 12 is fully separable from bottom portion 14 a securing means is provided to connect upper portion 12 to bottom portion 14 after absorbent 110 has been inserted into registration track or groove 22 of bottom portion 14. In the embodiment of device 40 the securing means is post 32 which is inserted into void or detent 34 and which is captured therein. Device 40 also includes a cutter portion 21 with teeth-like edges or serrations that serve to allow the user of device 40 to tear absorbent 110 from handle 114 of collector 106 when absorbent 110 has been captured between upper or top portion 12 and bottom portion 14.

It will be appreciated by those skilled in the art that devices 10 and 40, may involve the transfer of the identifying bar code 152b from the handle 106 of the collection device of FIG. 10 to sample holder 10 to provide the bar code shown in the position of bar code 26, however, it is possible to provide sample holder 10, 40 as a unit which includes a specimen collector such as collector 106, both of which devices are pre-provided with matching bar codes 26.

It also should be appreciated that the embodiments shown in FIGS. 1-5 involve modification of the structure of the device used to collect the sample. Specifically, the handle 114 is separated from paper 110 upon which the sample resides. While the embodiments of FIGS. 1-5 do not contain all the preferred features of a preferred embodiment, they will be functional for some purposes in which a chain of custody or evidentiary issues are not as strict as within criminal chain of custody matters.

Figure 12:
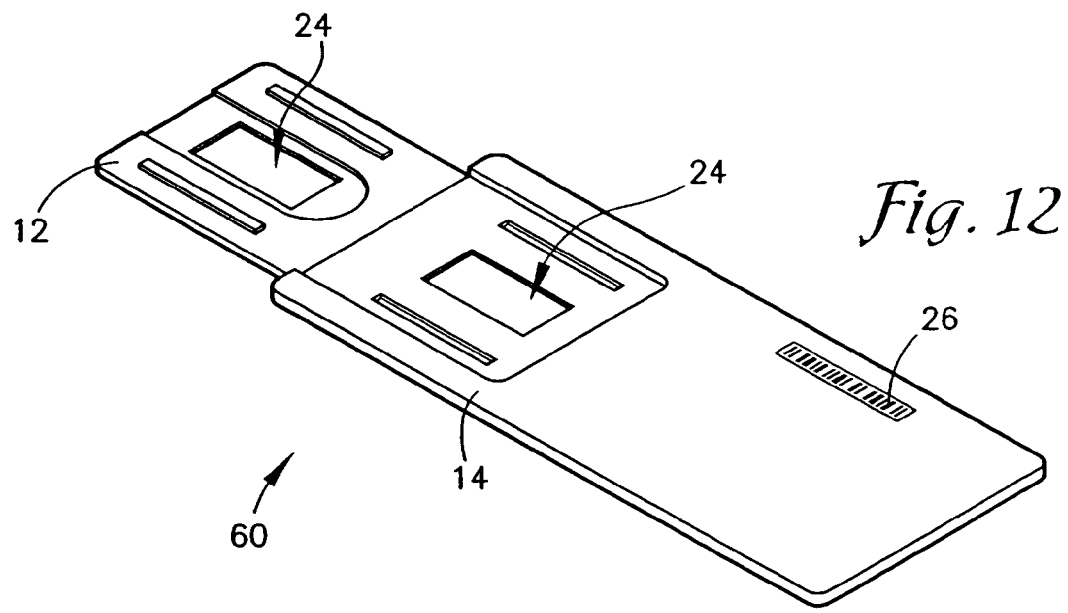
FIG. 12 shows the embodiment of FIG. 11 fully opened and with the collection absorbent and handle absent to reveal window 24 in bottom portion 14.

The embodiment, shown in FIGS. 6 and 7, now to be described, provides all the preferred objects. Referring now to FIGS. 6-7, a specimen holder 50 is shown in which the entire collection handle 114 and collection paper 110 of collection device 106 (FIG. 10) is inserted into the holder 50. Holder 50 is comprised of an upper portion 12 and a bottom portion 14 which can be superimposed on one another and pressed together to interconnect to capture device 106 (FIG. 12) within registration groove 22 of holder 50. Top portion 12 and bottom portion 14 are held together, as described for the embodiments of FIG. 1-5, by any useful means of securing the top portion 12 to the bottom portion 14. Such means may be adhesive tape, staples, ultrasonic fusing of the material together if the holder were plastic, or an arrangement of locking posts and detents can be utilized such as is shown in FIGS. 6-7. In the embodiment of FIGS. 6 & 7, posts 32 are registerable and insertably lockable into detents 34. It also will be appreciated that the handle 114 can be shortened, if necessary, to fit into the device by cutting the handle 114 or providing a perforation line that allows breaking handle 114 to shorten it to a length compatible with holder 50.

In operation, the function of the embodiment 50 of FIGS. 6 & 7 is as follows: A handle sample holder 106 having a bar code 152b and having a collection absorbent or paper 110 attached thereto such as the collection device 106 of FIGS. 8-10 of the present application is inserted into bottom portion or half 14 of device 50. As is shown in FIG. 6, windows 52a, b and 54a, b are included on both top portion 12 and bottom portion 14 of holder 50. A support band 56 bridges windows 52a, b and 54a, b. Support band 56 supports device 106 within the holder 50 while allowing the bar code 152b on device 106 to be viewed and read with a bar code scanner and sample collection portion 110 of device 106 to be exposed and accessible and viewable at all times.

It will be appreciated that during manufacture, bottom portion 12 and top portion 14 of device 50 can be constructed so the top and bottom portions are identical. Thus, the individual inserting device 106 into the halves of the device need not select and match a top portion and a bottom portion. This can be achieved by simply manipulating the closure method so the top 12 and bottom 14 can be the same. In the case of the posts and detents, it would be possible to put all the posts on either the top or the bottom or on one edge of the device so identical tops and bottoms could be constructed.

In operation, after device 106 has been inserted into holder 50 and top portion 12 connected to bottom portion 14, the resulting assembly is as shown in FIG. 7. In FIG. 7, device 106 is locked within the compressed together top and bottom halves 12, 14 of device 50 and bar code 152b of device 106 is visible within window 52a and collection paper 110 is visible and accessible through window 54a, b. It will be appreciated that as window 54a is aligned with window 54b that a portion of collection absorbent 110 may be removed by use of a punch to extract a sample of collection paper or absorbent 110 for testing. In addition, it will be appreciated that the original bar code attached to sample collection device 106 is still attached to device 106 and is visible through window 52a of device 50. Further, if additional or alternate bar code or identification symbols are needed, they may be placed on device 50 as is shown by bar code label 26.

Figure 11:
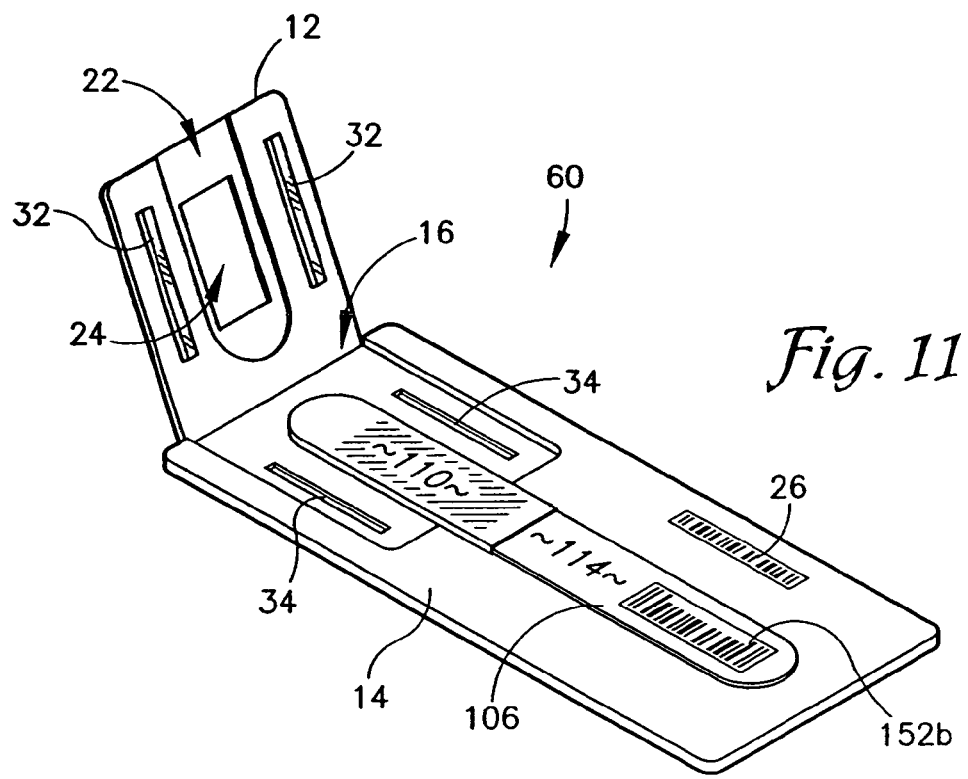
FIG. 11 is a top and front perspective view of another embodiment of the specimen holder designed to receive the entire collection absorbent and attached handle and showing the hinged lid 12 aligned for capture of the absorbent 110 by the device.

Referring now to FIG. 11, yet another embodiment of the holder, holder 60, will be discussed. Holder 60 is comprised of a holder bottom or body portion 14 to which is attached a foldable, closeable top portion or hood portion 12 and which is attached to body portion 14 at hinged edge 16. Attachment point or edge 16 can be any flexible hinge type of connection between body 14 and hood 12 which permits hingeable opening of portion 12 with respect to body 14. Alternatively, it will be appreciated by those skilled in the art that portion 12 could be a separate cover from body portion 14 and the two portions 12 and 14 made connectable by interlocking weld means or post and detent means or other connection means as previously described for the devices shown in FIGS. 1-7. Again, the object is to contain a collection device 106 within holder 60 while presenting the identifying bar code 152b and the sample collection paper or portion 110 visible and available for reading and for the punching of sample disks from collection paper 110.

In operation, device 60 of FIG. 11 is used as follows. A collection sample device such as device 106 of FIGS. 8-10 is placed on bottom portion 14 so that absorbent 110 covers window 24 on bottom 14 and handle 114 of device 106 is generally flush with the surface of bottom portion 14. Window 24 permits collection paper 110 to be viewed and paper disks to be punched from collection paper 110 when device 106 is mounted within holder 60. It will be appreciated that window 24 of top portion 12 of the device 60 has a similar window portion 24 directly opposite and in registration with the window of top 12 and which is in base portion 14. This alignment of windows 24 permits a paper disk to be punched from collection paper 110 as absorbent paper 110 is held within device 60. Further, the disk can fall out of holder 60 through window 24 in bottom portion 14 and into testing vial or dish.

It will be appreciated that when top portion 12 is pressed downwardly against base portion 14, the previously described securing means for securing device 106 within device 60 may be used and that top portion 12 cannot be opened or separated from base portion 14 without the tampering or the attempt to open being evidenced. In this manner, the chain of custody and evidentiary requirements are retained. Device 106 is adapted for use in an automated sampling machine without the need to separate collection paper 110 from handle 114 or the need to transfer identifying bar code 152b from device 106 onto a automated sampling holder device.

Figure 13:
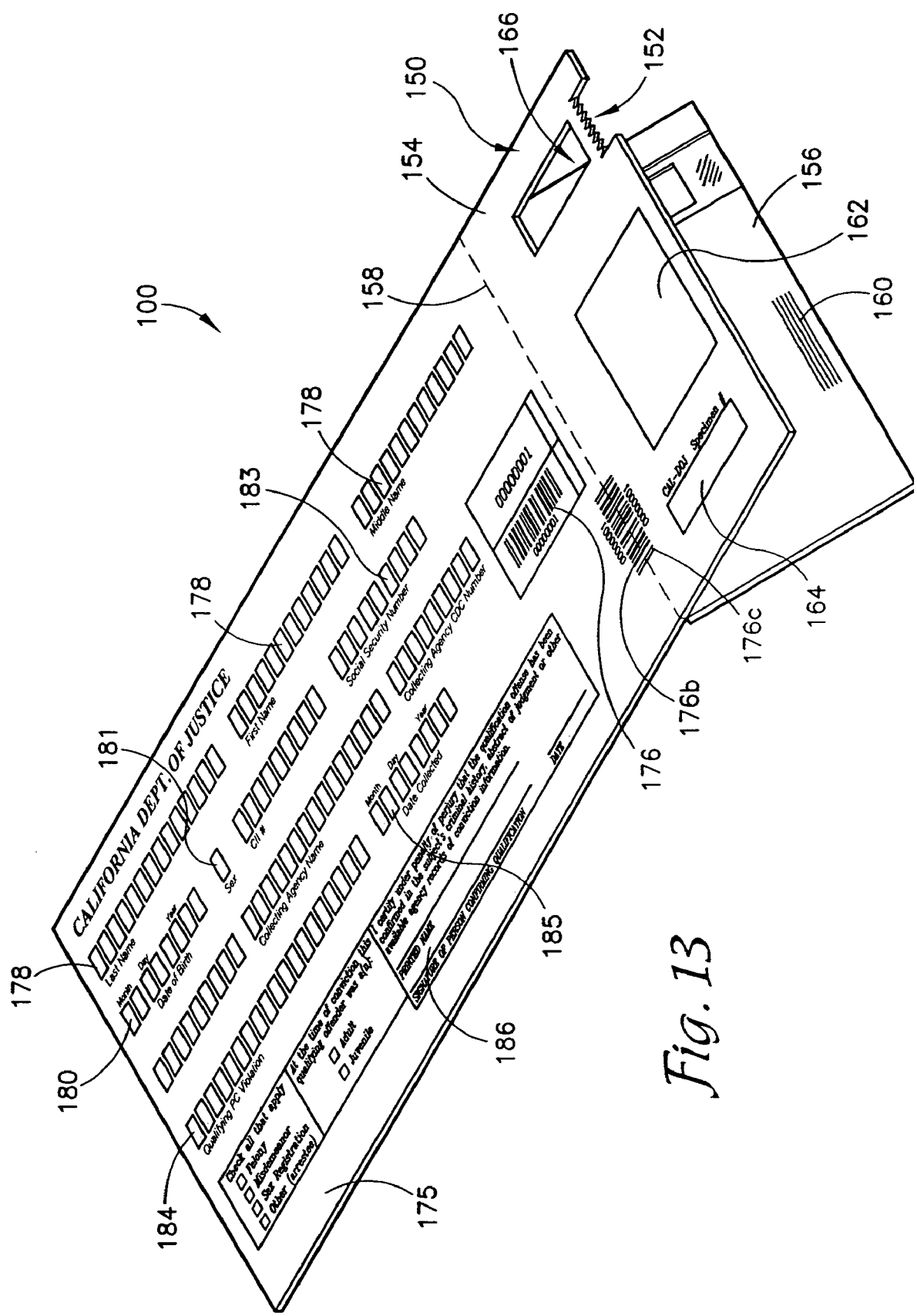
FIG. 13 is yet another embodiment of a specimen holder having an information card 175 attached thereto and with the specimen holder portion 150 opened to receive a collection absorbent or paper therein.
Figure 14:
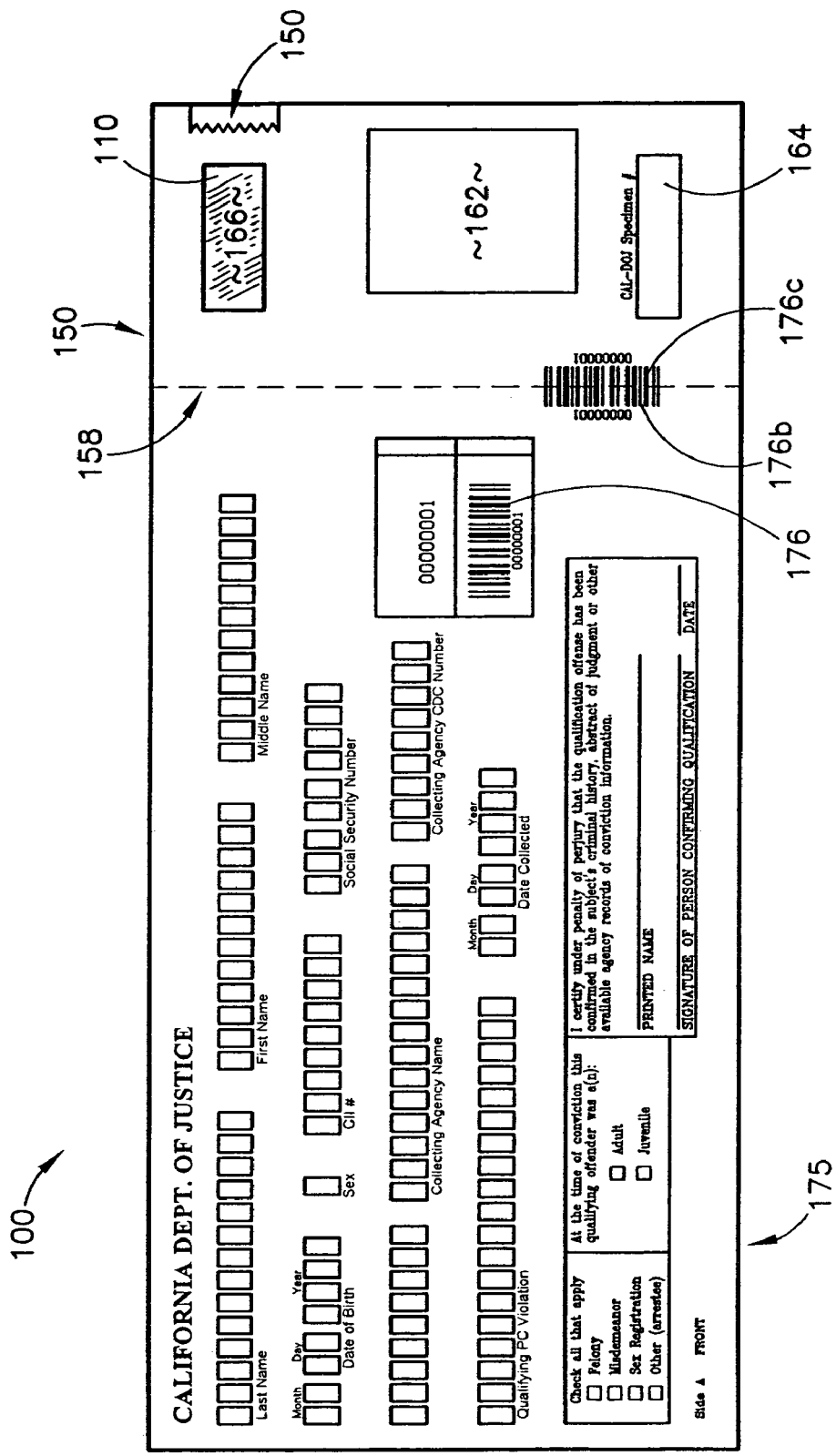
FIG. 14 is a top plan view of the embodiment of FIG. 13 showing absorbent 110 captured within window 166.
Figure 15:
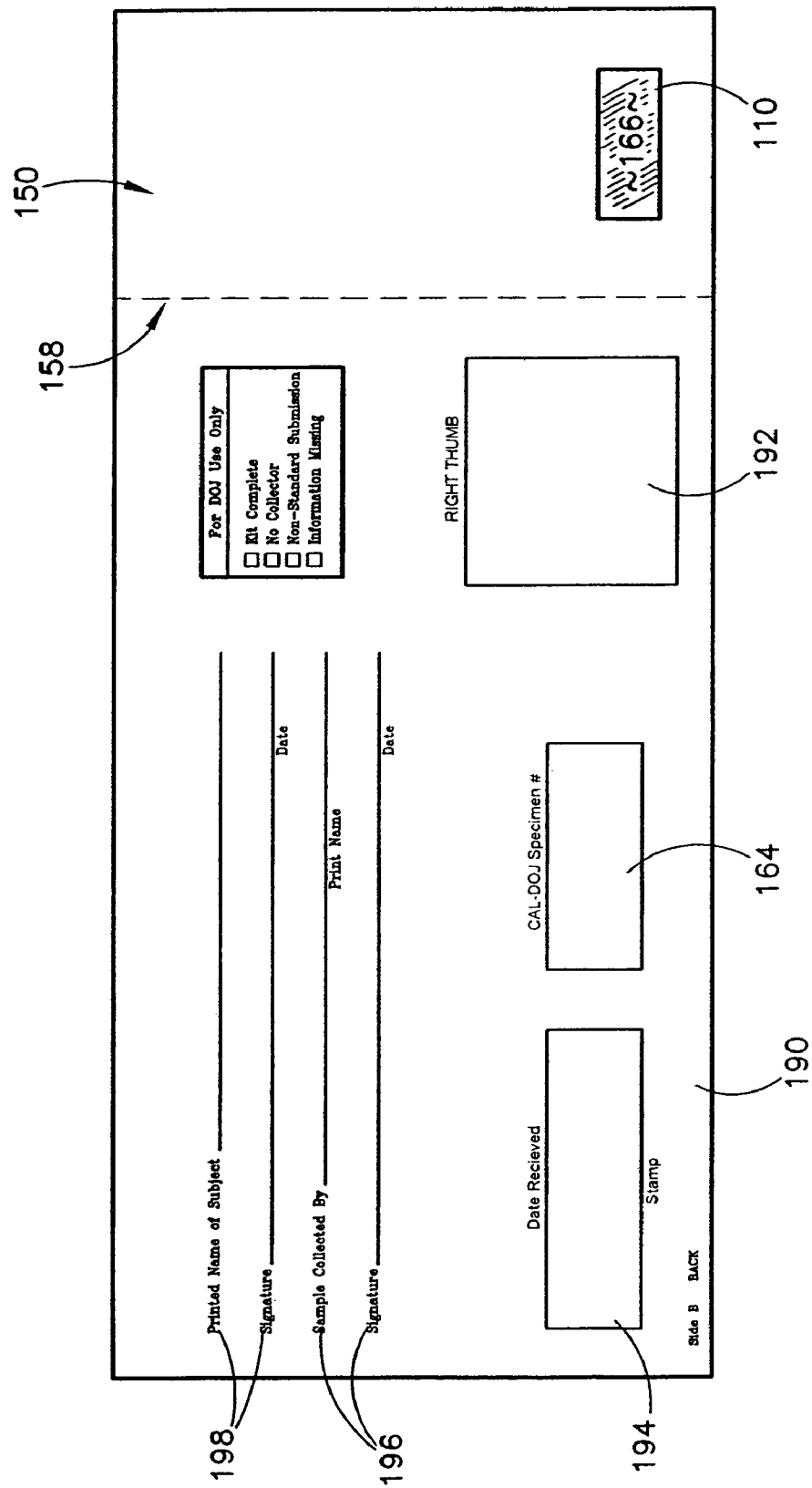
FIG. 15 shows the reverse side of the embodiment of FIG. 13 and showing window 166 on the reverse side of the embodiment with absorbent 110 captured therein.

Referring now to FIGS. 13-15, a collection card 100 is shown having an embodiment of the specimen collection holder 150 attached thereto. The specimen holder 150 may be used alone in addition to being used, as shown, attached to information portion 175. Card 100 is comprised of an information portion 175 on which may be recorded the name 178, date of birth 180, sex 181, social security number 183, and other useful information regarding a suspect or convict such as the violation which qualifies for obtaining a biological specimen 184, and the date of collection 185, and the signature of the individual certifying that the offense for which the specimen was collected qualified as an offense which permitted the collection of biological information 186, and for which a blood or fluid or DNA specimen and other evidentiary information is to be obtained. The specimen can be collected in the manner previously described by use of a handle portion 106 having a collection paper 110 attached thereto. The paper may then be inserted into holder 150 which operates in a manner similar to the manner described previously for the embodiment shown in FIGS. 1-5 wherein the collection paper 110 attached to handle portion 106 is inserted into the holder 150 such that the paper is located in window 166. In the present embodiment, handle 114 is removed through the use of serrations 152 provided with the holder 150. Specifically, in the embodiment of FIGS. 13-15, collection paper 110 would be inserted into holder 150 in between upper portion or surface 154 and lower portion or surface 156, and upper surface 154 is then closed against lower surface 156 in the manner previously described herein to secure surface 154 against surface 156 and capture absorbent sample collection paper 110 therebetween using adhesive strip 160. Once the surfaces are secured together to contain specimen collection paper 110 therebetween, the cutter or serrations 152 may be used to separate handle 106 (FIG. 10) from collection paper 110.

In the embodiment of FIGS. 13-15, bar codes 176 are provided both on information portion 175 and on holder portion 150. In one embodiment, a bar code 176b, 176c is provided which spans across both information portion 175 (See, bar code 176b) and holder portion 150 (See, bar code 176c) such that if holder portion 150 is separated from information portion 175 by the use of perforation 158, both portions 175, 150 will contain an identical bar code identification 176 as it is printed to span perforation line 158.

An additional aspect of evidence which can be obtained by the use of the embodiment of FIGS. 13-15, is a fingerprint of the suspect or convict which can be placed into fingerprint block 162 which is on holder top portion 154. By the use of the embodiment shown in FIGS. 13-15, a law enforcement department can obtain all relevant and necessary information to identify a suspect or convict or other offender by the use of body fluid sample or DNA as well as by conventional forms of identification such as fingerprinting into block 160 and with identifying information placed into information portion 175 and a split bar code 176b, 176c correlating the physical evidence of holder portion 154 with the suspect information contained on information portion 175. A separate block 164 for imprinting a state department of justice identifier also is provided.

In FIG. 15 the reverse side of embodiment 100 is shown, including the reverse side 190 of information portion 175 and the reverse side 200 of holder portion 150. On the reverse side of the information portion areas for marking the date the card 100 was received at various locations 194 is provided, a space for a department of justice specimen number 164, identification and signature of the collecting agent 196 the name and signature of the subject 198 and space for a second fingerprint 192. The second finger print can further serve as a correlating marking proving that the individual whose biological sample and/or finger print appeared in holder 150 also was available to provide the finger or thumb print which was placed on the reverse side 190 of information portion 175.

Figure 16:
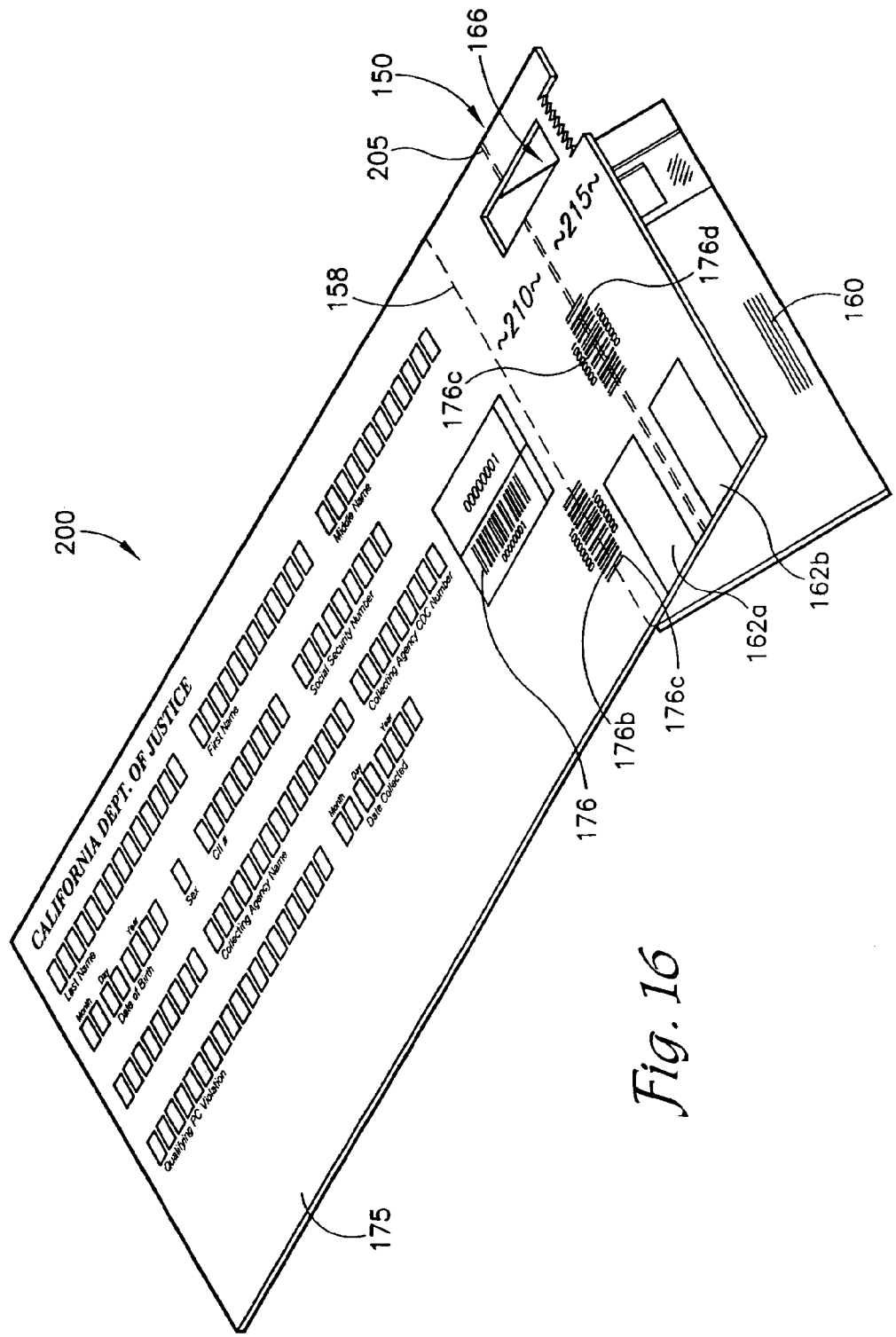
FIG. 16 shows a top and right side perspective view of an alternate embodiment of the holder having an information sheet 175 attached thereto and showing a holder portion 150 which can be subdivided into two portions 210, 215 each containing a portion of the absorbent paper captured within window 166 and each bearing one half of the identical bar code 176c', 176d which matches the identical bar code 176b, 176c and 176.
Figure 17:
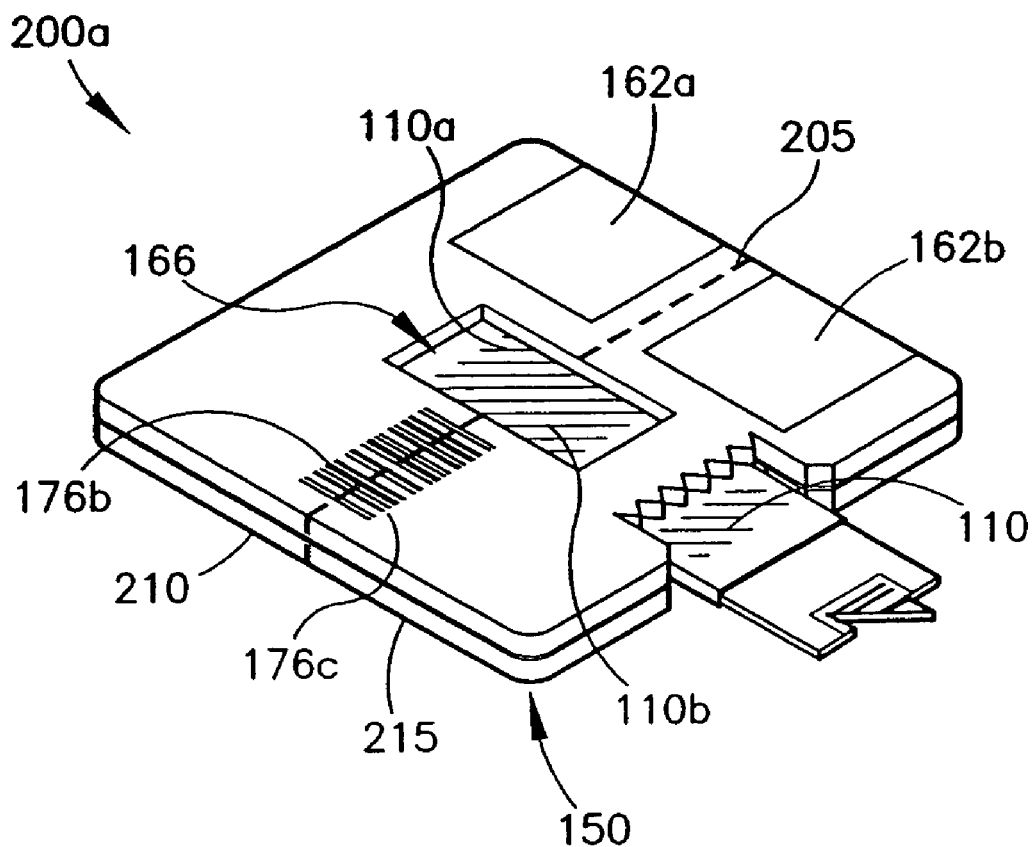
FIG. 17 is a top front and right side perspective view of a specimen or collection paper holder which may be subdivided into two portions each holding a portion of sample 110a, 110b therein distributed between halves 110, 115.

Referring now to FIGS. 16 and 17 alternative embodiments 200, 200a are presented. In the embodiment of FIG. 16, a perforation line 158 is shown in the location described in the discussion of the embodiment of FIGS. 13-15. In the embodiment of FIG. 16, perforation line 158 allows separation of holder portion 150 from information portion 175 as was the case for the embodiment shown FIGS. 13-15. The embodiments shown in FIGS. 16 and 17 also contain a second perforation line 205 which serves to subdivide the sample holder 150, and the evidence contained thereon, into multiple sample portions 210, 215. This splitting of sample holder 150 into two sections 210, 215 permits separation of the biological specimen 110 (FIG. 17) and/or fingerprint evidence to be split into two portions. In the case of absorbent 110 (FIG. 17) is can be split into two portions 110a and 110b. This splitting permits a portion of the identical biological sample, for example, 110b, to be sent to a laboratory for analysis while a portion 110a is retained with the information portion 175 (FIG. 16) of the embodiment.

In the embodiment of FIG. 16, a bar code 176, 176b, 176c, 176c', 176d is affixed to each portion of the embodiment with some representations of the bar code 176b, 176c, 176c', 176d spanning two of the sections. As has been previously described, bar code 176b, 176c is placed across perforation 158 such that a portion of the bar code 176b, which is fully readable, remains with information portion 175, and a portion of the bar code 176c, which is fully readable, is retained with holder portion 150. In the embodiment shown in FIG. 16, which holder portion 150 can be split into two portions 210, 215 by use of perforation line 205, a second bar code 176c', 176d is placed across perforation line 205 to permit identification of both halves of holder portion 210, 215 once perforation line 205 has been used to divide holder portion 150 into two halves 210, 215. It also will be appreciated that as the holder portion 150 of embodiments 200, 200a is separable into first and second halves 210, 215 that two fingerprint areas 162a, 162b are provided on each half 210, 215 of holder portion 150. It will be appreciated by those skilled in the art that it will be desirable in most cases that bar code 176c', 176d be identical to bar code 176b, 176c and to bar code 176. Alternatively, a separate bar code number for holder portion 215 could be cross-indexed against the bar code used for holder portion 210 as the intent is to be able to match holder portion 210 with holder portion 215 once separation using perforation line 205 has occurred.

It will be appreciated by those skilled in the art that an embodiment similar to those shown in FIGS. 1-3 and 11-12 could be devised in which the hinge connecting the top half to the bottom half is located along the side of the device and parallel to paper 110. In this configuration, a hinged embodiment could be provided which allows the sample or absorbent 110 to be split into two absorbent portions as is provided for in the embodiments of FIGS. 16 and 17.

Now, more particularly referring to the embodiment of FIG. 17, a variation on the embodiment of FIG. 16 is shown in which device 200a is provided with a perforation line 205 which divides device 200a into two pieces. A bar code 176b, 176c is provided which is centered on perforation 205 to provide a bar code 167b, 176c with a first half 210 having bar code 176b thereon and with a second half 215 having bar code 176c when perforation 205 is used to divide device 200a into first and second halves. A portion of collection paper 110, specifically 110a, is allocated to first half 210 and a second portion of collection paper 110b is allocated to second half 215 when perforation 205 is used to divide device 200a into two pieces. If desired, additional evidence regarding the subject person can be provided in the form of fingerprints which would be applied to fingerprint area 162a, 162b. Device 220a can be associated with a separate information portion 175 (FIG. 16) or can be attached to an information portion 176 by use of an adhesive.

Figure 18:
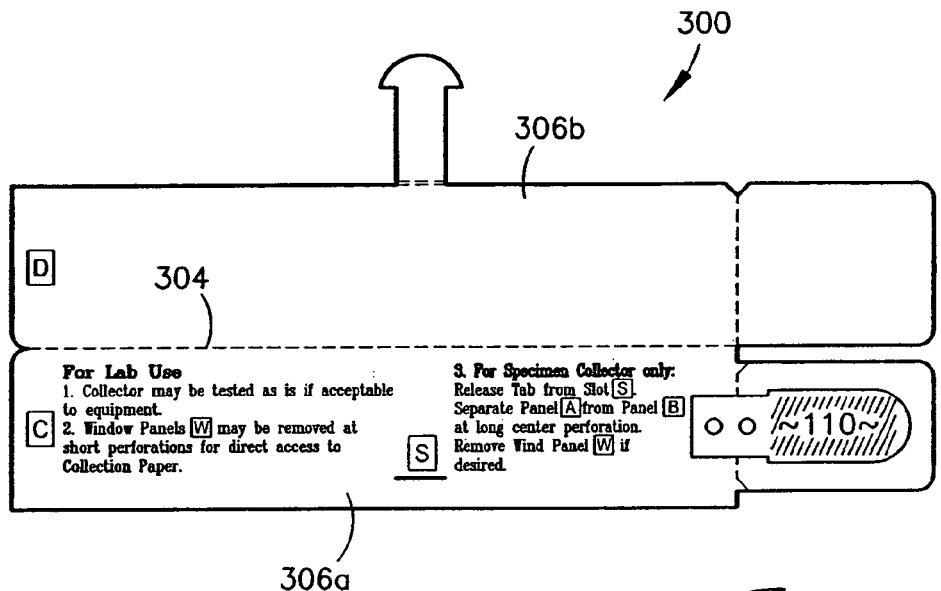
FIG. 18 is a bottom plan view of a combined sample collection device and holder which may be used for swabbing a blood drop sample from a subject.
Figure 19:
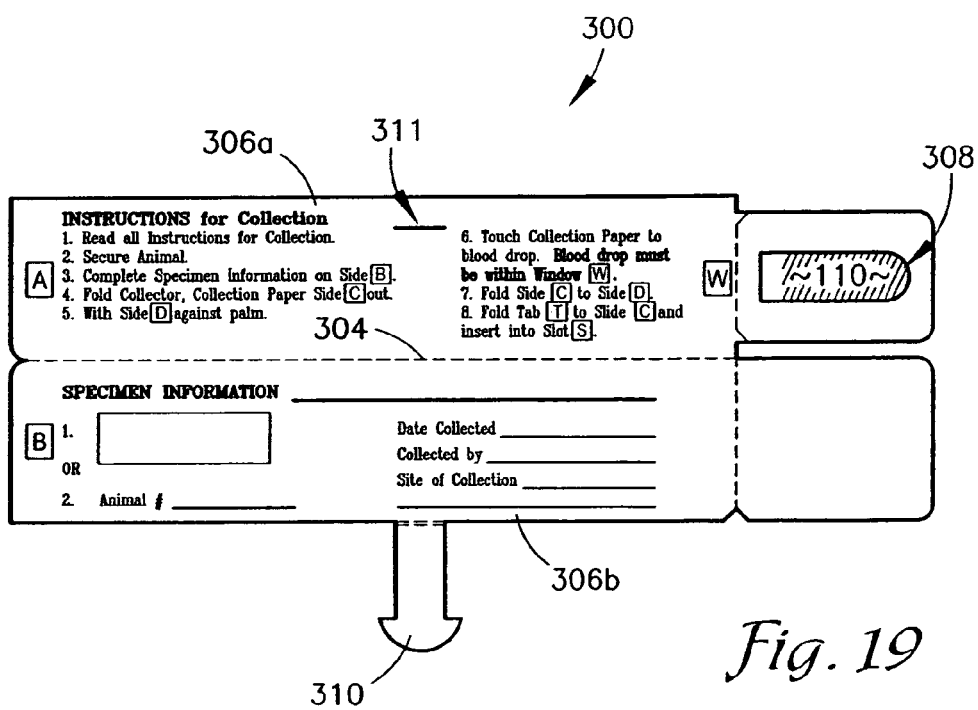
FIG. 19 is a top plan view of the embodiment of FIG. 18 and showing the absorbent 110 within window 308.

Referring now to FIGS. 18 and 19 another embodiment of a specimen collection device is shown in which the collection absorbent or paper 110 is pre-attached to the holder. Referring first to FIG. 18, device 300 is comprised of handle 306a, 306b. Handle half 306b may be folded onto handle half 306a along perforation or fold or crease line 304 which permits handle portion 306b to cover and protect paper 110 which is at one end of handle portion 306a. It will be appreciated that information regarding the sample and the individual from whom the sample is taken and the time and other identifying and informational indicia may be recorded on any of the four surfaces of handle 306a, b as shown in FIGS. 18 and 19. Device 300 is provided with a sampling window 308 through which paper 110 is exposed to allow the punching of a specimen of the blood drop or saliva that has been placed onto paper 110.

In operation, device 300 may be used for obtaining a blood sample from an animal such as by first securing the animal, followed by completion of the specimen information on side b of handle portion 306b to identify the animal. After side b of handle portion 306b has been filled out, handle 306a is folded against handle portion 306b such that folded to the outside. This manner of folding will present the whole of collection paper 110 for collection of the specimen with window 308 on the inside of the fold. The user will place side d of handle portion 306a against the palm and swipe paper 110 against the blood drop that is formed where the animal's ear has been pricked. Once sufficient blood has been collected to fill the area that is framed by window 308, side d of handle portion 306b is folded against side c of handle portion 306a to place side a of handle portion 306a and side b of handle portion 306b to the outside at which time tab 310 may be inserted into slots 311 to maintain the device in a closed position. Alternatively, an adhesive strip having a releasable cover on it may be placed on side d of handle portion 306b to permit the device to be closed adhesively.

Figure 20:
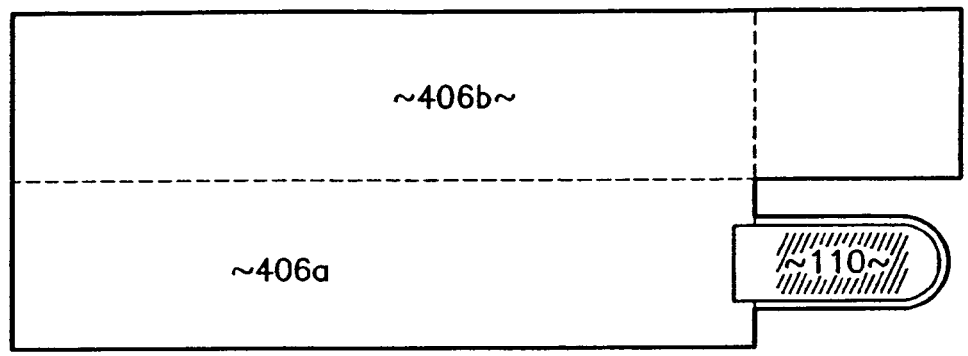
FIG. 20 is a top plan view of an alternate embodiment of a combined specimen collection device and holder showing absorbent 110 extending therefrom.
Figure 21:
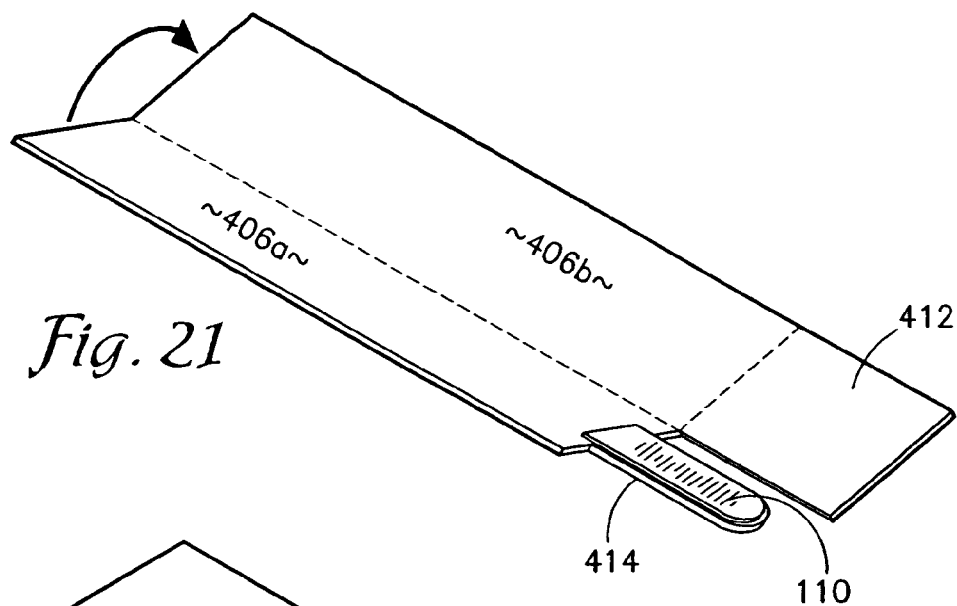
FIG. 21 shows the collection device of FIG. 20 partially closed and showing absorbent 110 supported on extension or back cover 414.
Figure 22:
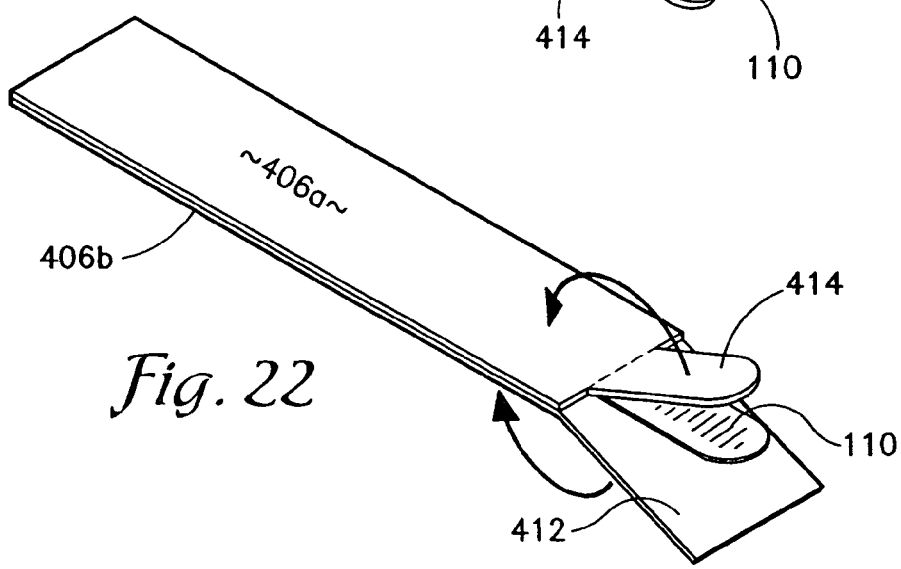
FIG. 22 shows the embodiment of FIG. 20 fully closed and with back cover 414 and front cover 412 partially folded back from absorbent 110 to expose absorbent 110 for punching of a sample therefrom.

Referring now to FIGS. 20-22, another embodiment, 400, similar to the embodiment shown in FIGS. 18 and 19. FIGS. 20-22 showing the folding together of handle 306a and 306b together and which is similar to the folding together of handle 306a, b shown in FIGS. 18-19 for embodiment 300. The embodiment of FIGS. 20-22 is an embodiment that lacks window 308 (FIG. 19) to provide access to collection paper 110. Rather, the embodiment of FIGS. 20-22 provides greater protection for paper 110 by providing a front cover 412 and back cover 414 for paper 110 before and after the sample is taken. In FIG. 22 handle 406a, b of embodiment 400 is shown in the closed position with front cover 412 separated from paper 110 and back cover 414 separated from paper 110. Front cover 412 and back cover 414 are made separable from paper 110 to permit paper 110 to be exposed for sample taking and to permit paper 110 to be exposed in the laboratory for punching from paper 110 of a sample for testing purposes. On embodiment 400, information may be recorded on the outside of handle 406 as shown in FIGS. 18-19 form device 300.

When it is desired to use the device shown in FIGS. 20-22, either front cover 412 or back cover 414 may be folded backwardly to fully expose paper 110 leaving the other cover in place to support paper 110 as it is rubbed against the subject for a DNA specimen collection or used to blot blood for a blood specimen. Once the specimen has been collected, the folded cover 412 or 414 can be replaced to cover and to protect the sample which has been collected onto sample collection paper 110. It will be appreciated that when covers 412, 414 are in the closed position they cover and protect collection paper 110. Alternatively, the sample can first be collected onto paper 110, followed by the closure of handle portions 406a, b by folding handle portion 406a against 406b to cover and protect collection paper 110 until the sample reaches the laboratory. When the sample reaches the laboratory, front cover 412 and back cover 414 can be torn away from handle 406a, b thus exposing collection paper 110 for extraction of a sample portion therefrom for use in testing.

Figure 23:
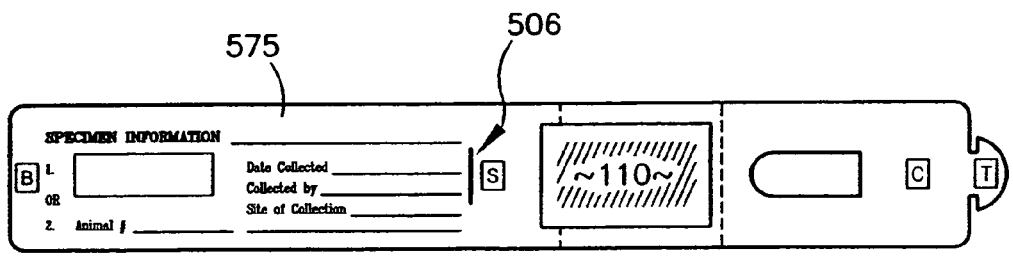
FIG. 23 shows a top plan view of yet another embodiment of a specimen sampling device and holder and showing absorbent paper 110 mounted thereon.
Figure 24:
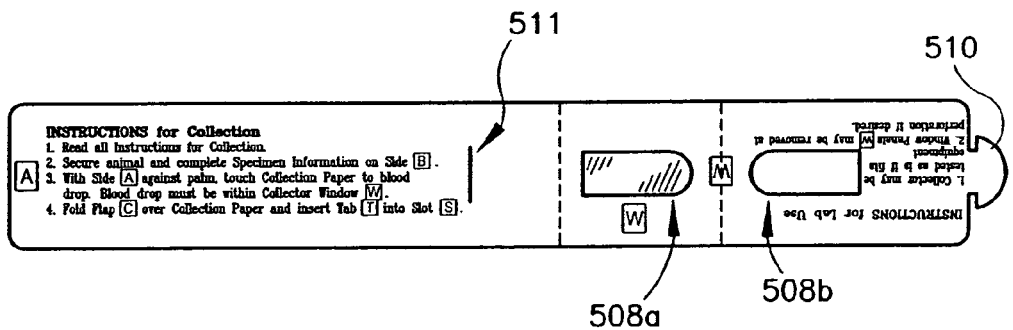
FIG. 24 shows a bottom plan view of the device of FIG. 23.

Referring now to FIGS. 23 and 24 yet another embodiment of a collection device 500 will be described. Device 500 is provided with a punch window 508a, b to allow a specimen sample to be punched from specimen collection paper 110. Device 500 presents a handle portion 506 having an information portion 575 thereon for use in identifying the subject, such as a particular animal. When it is desired to use device 500, the user fills in the information about the subject animal on information portion 575. The user then pricks the ear of the animal and touches paper 110 to the drop of blood that is formed on the ear. The best practice in the use of device 500 is to apply sufficient blood so that the paper 110 exposed via window 508a is fully saturated with blood. In this regard the blood can be applied to paper 110 from side B of handle 506 of from side A of handle 506. Once the blood has been applied to the device end portion C is folded along line W and away from side A and against side B. In this manner end portion C cover paper 110 on side B and paper 110 is the framed on each side of device 500 by window 508a on side A and by window 508b on side B. This allows the operator at the testing laboratory to have a clear, supported field of paper 110 from which to punch a testing sample.

Figure 25:
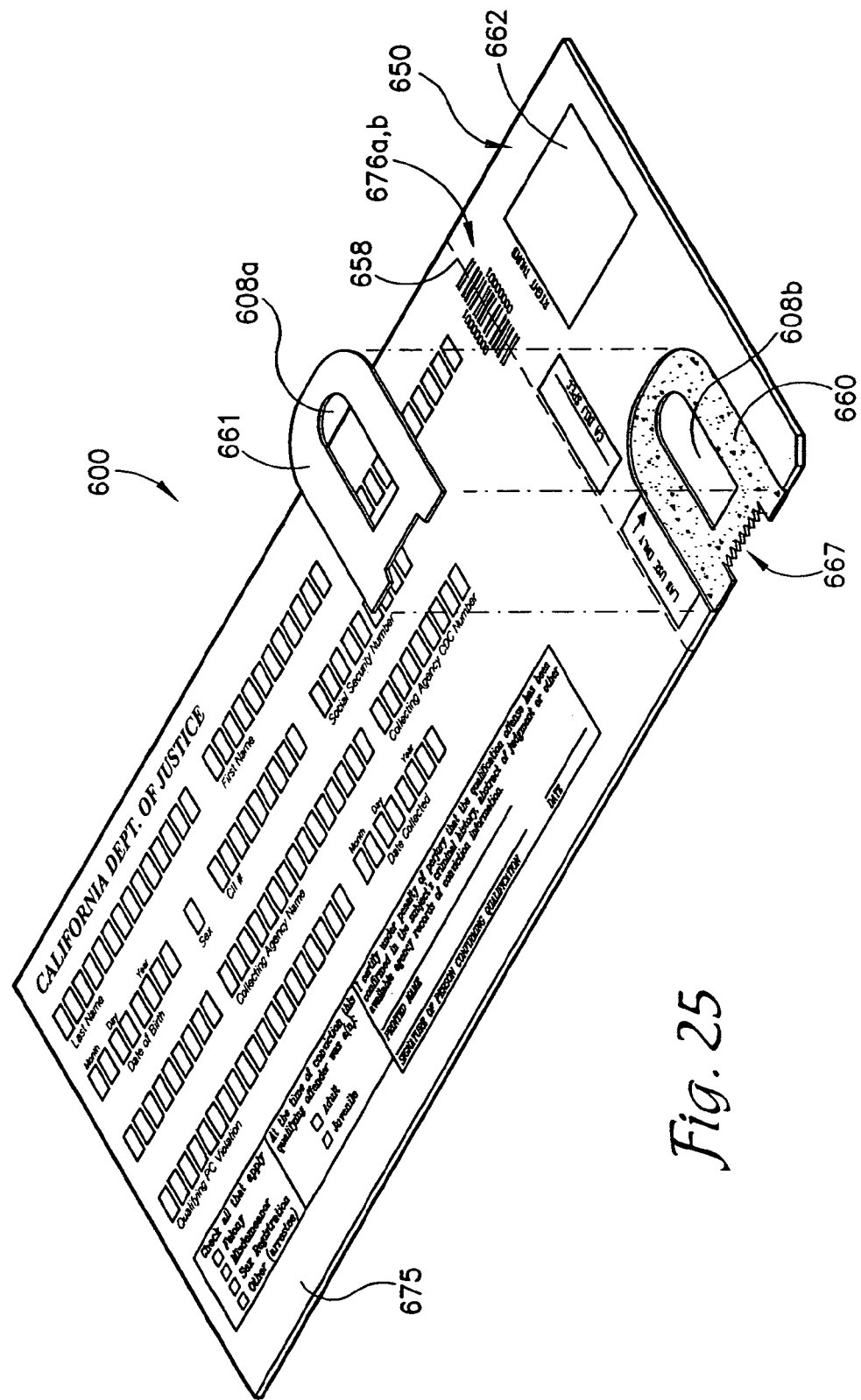
FIG. 25 shows another embodiment of a collection paper or specimen holder 650 with an information portion 675 attached thereto and adhesive stripper portion 661 aligned for application to holder 650 to capture an absorbent therebetween.

Referring now to FIG. 25, yet another embodiment of the evidence collection device is shown. Device 600 is a combination of an information portion 675 and a specimen holder portion 650. As previously described, information portion 675 is to be filled out at the time the specimen is being acquired. Specimen holder portion 650 contains the various pieces of evidence which are being collected such as a fingerprint in area 662 and an area for insertion of collection paper 110 (not shown) which is placed onto area 660 and to which an adhesive backed curing paper 661 is then applied to secure collection paper 110 to specimen holder 650. It will be appreciated that device 600 contains window 608a, 608b through which the laboratory may punch a testing sample from paper 110. As in previous embodiments of this invention, device 608 is provided with a cutter edge 667 which can be used to separate absorbent paper 110 from handle 114 (FIG. 10). Device 600 further contains bar code 676 which is printed across perforation 658 to provide an identifying bar code on both information portion 675 and specimen holder portion 650.

Figure 26:
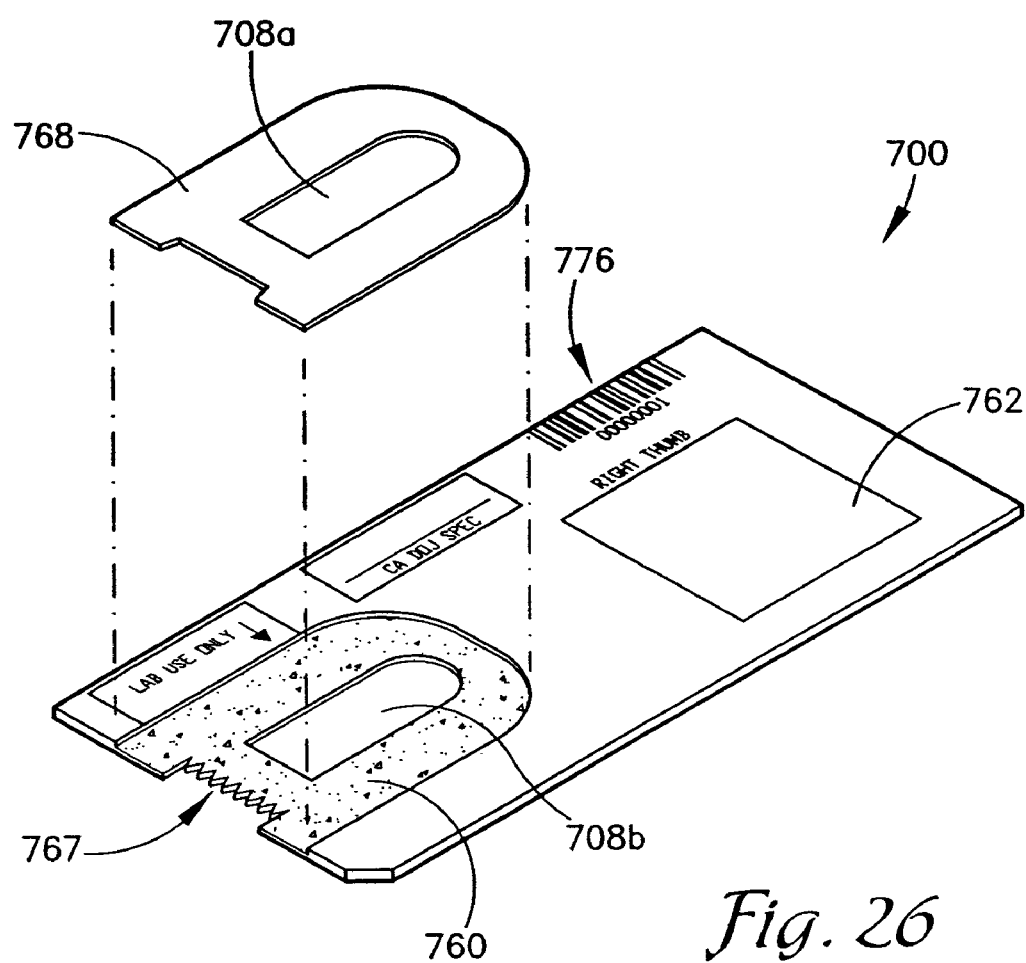
FIG. 26 is a front and right side perspective view of a holder similar to the embodiment of FIG. 25 but having no information card attached thereto.

Referring now to FIG. 26, a device 700 similar to device 600 of FIG. 25 is shown. Device 700 is a specimen holder only which may be affixed to a separate information identification card or may simply be used within the laboratory to hold a specimen for insertion into an automatic testing device. Device 700 is comprised of substantially the same features as is device 600. A bar code 776 is provided for identification of device 700. A thumbprint may be applied to device 700 area 762 when device 700 is used in the field. A collection paper 110 may be aligned within paper holder area 760 to cover window 708b after which an adhesive securing paper or adhesive label seal 761 is applied to secure paper 110 in holder 700. Adhesive strip 761 is provided with window 708a which allows the laboratory to punch a sample from paper 110 which is secured within device 700. Again it will be appreciated that device 700 is provided with cutter teeth 767 which allows separation of paper 110 from handle 114 (FIG. 10).

Figure 31:
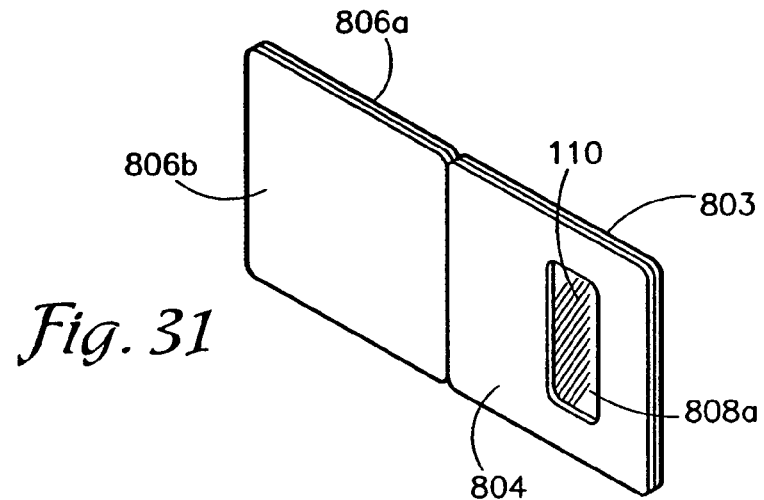
FIG. 31 shows the device of FIG. 27 fully assembled with sides 806a, 806b joined together to form a handle portion for holding the device while a sample is applied to absorbent 110.

Referring now to FIGS. 27-31, yet another embodiment of the present invention will be described. Device 800 is shown in FIG. 27 in its nearly collapsed form. In FIG. 27, device 800 is shown with an adhesive seal 802 removed and handles 806a, 806b partially separated from collection paper holding panel 803 and window panel 804. It will be appreciated that device 800 is essentially an elongate rectangle of paper which has been folded to present four panels, to handle panels or portions 806a, 806b and paper holding panel 803 and window panel 804. Examination of FIG. 29 shows that the reverse side of panel 803 from that shown in FIG. 28 contains window 808b. Referring now to FIG. 28, device 800 has been expanded further from the nearly closed position shown in FIG. 27. In FIG. 28, various portions of the device are easily seen. Handle portion 806a is connected to window panel 804 which is connected to paper holding panel 803 which is connected to handle 806b. On handle 806a, an adhesive section with release liner 807 is provided which will allow the securing of handle 806a to handle 806b to prepare the device for use. In FIG. 29, device 800 is shown from the reverse face of that shown in FIG. 28. In FIG. 29, it can be observed that absorbent paper 110 is visible through window 808b in paper holder section 803. It will also be appreciated that window 808a and at window 808b align when panel 803 is brought against panel 804 along Arrow J. This alignment of windows 808a and 808b provides a space for the laboratory operator to cleanly punch a sample from collection paper 110 without obtaining any other portions of device 800 during the punching process. Referring now FIG. 30, panel 804 has been positioned against panel 803 and handle portion or panel 806a is about to be then positioned against handle portion 806b. It will be appreciated that adhesive release liner 807 has been removed so that handle 806a can be secured to 806b. Referring now to FIG. 31, device 800 is shown fully assembled with handle portion 806a adhesively secured against handle portion 806b and handle 808a aligned with window 808b to allow absorbent paper 110 to be exposed for collection and punching purposes. Device 800 is then used in collection devices shown in FIGS. 18-24 when collecting paper is applied to the pricked ear of an animal or has blood or saliva or other body fluid applied to it to collect biological specimen of the subject or animal for later testing.

Figure 33:
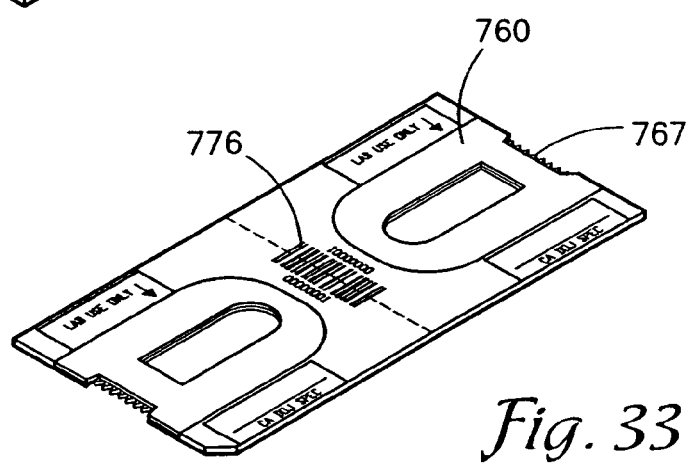
FIG. 33 shows a plan view of an embodiment of the present invention having dual collection absorbent holders each having a cutter and a cover portion having an adhesive thereon to permit capture of the absorbent within the device and having a portion for recording of a finger print thereon with the cover show affixed in the figure.

Referring now to FIG. 33 a alternate embodiment of the device shown in FIGS. 25 and 26 is shown. In the embodiment of FIG. 33 two sample storage portions 760 are shown. The dual sample storage portions allow the collection agency to collect two different specimens (e.g., saliva and blood) from the same subject or duplicate samples (e.g., two saliva samples) from the same subject. As in the devices of FIGS. 25 and 26 the specimen absorbent is secured onto portion 760 by application of an adhesive-backed cover paper 661 as previously described.

Figure 32:
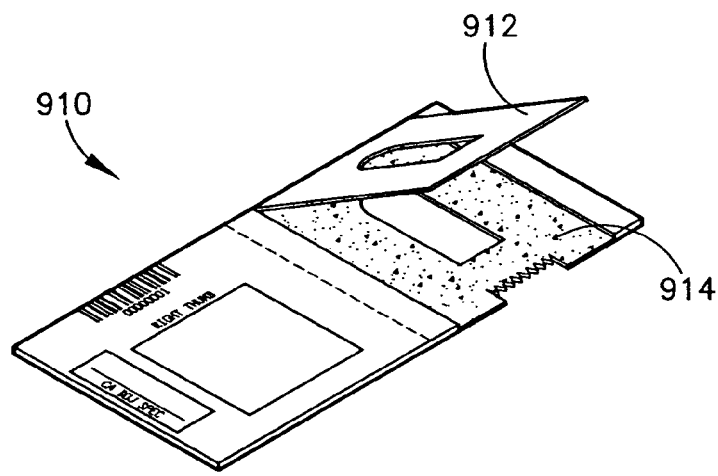
FIG. 32 shows a plan view of an embodiment of the present invention having a portion for holding a collection absorbent with a cover portion having an adhesive thereon to permit capture of the absorbent within the device and having a portion for recording of a finger print thereon.

Referring now to FIG. 32 yet another alternate embodiment 910 is shown in which top layer 912 is shown in a peeled-up position to allow insertion of a collection absorbent 106 therein. Once the absorbent, having the sample thereon has been inserted into the device the top layer can be pressed against bottom layer 914 to capture the collection absorbent therebetween. In one embodiment a releasable adhesive is used to secure top layer 912 to bottom layer 914. Alternatively, a release liner (not shown) can be used to cover a permanent adhesive on bottom layer 914 until it is desired to secure top layer 912 to bottom layer 914 at which time the release liner can be removed to expose the adhesive. The use of a release liner is preferred in situations in which it is desired to permanently secure the collection absorbent into the device 910 and to reveal any attempt to re-open the device to tamper with the absorbent once it is placed into the device.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

Having now described the features, discoveries and principles of the invention, the manner in which the inventive oral fluid collection device is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

I claim:

1. A combination crime evidence specimen absorbent collector and crime evidence specimen holder into which the absorbent collector is secured to maintain evidentiary chain of custody requirements over a collected crime evidence while providing unobstructed access to said absorbent collector to permit removal of a portion of said absorbent collector having said collected crime evidence thereon from the absorbent collector for conducting of crime evidence analysis on the portion of said absorbent, the combination comprising:
   a specimen collector comprising a collector absorbent connected to a handle the handle permitting manipulation of said collector absorbent during evidence collection,
   a crime evidence specimen collected on said specimen collector,
   a specimen holder comprising an upper portion and a bottom portion for connection to said upper portion,
   means for tamper proof securing of said upper portion to said bottom portion,
   a registration track in said holder said registration track configured to register with the shape of said collector absorbent upon insertion of said collector absorbent between said upper and bottom portions,
   a cutter formed on said holder said cutter positioned adjacent said registration track for alignment of said collector absorbent with said cutter for separation of said handle from said collector absorbent by said cutter upon said securing of said absorbent in said holder, and
   a first void in said upper portion in unobstructed registration with a second void in said bottom portion said first and second voids being located on said upper and bottom portions to position said collected biological specimen of said absorbent collector therebetween to expose said collected crime evidence specimen within said voids to permit unobstructed removal through said registered first and second voids of a sample portion of said collected crime evidence specimen from said absorbent collector.

2. The device as claimed in claim 1 further comprising a subject information portion connected to said holder for recording information about subject from which said crime evidence specimens is collected.

3. The device as claimed in claim 1 wherein said securing means comprises a detent and projection for frictional capture of said projection in said detent.

4. The device as claimed in claim 1 wherein said securing means comprises an adhesive.

5. The device as claimed in claim 1 wherein said securing means comprises a staple.

6. The device as claimed in claim 1 further comprising an identification indicia on said holder.

7. The device as claimed in claim 1 wherein said upper portion is connected to said bottom portion with a with a hinge.

8. The device as claimed in claim 1 further comprising a separation line extending across said upper portion and said bottom portion and bisecting said first and second voids for separation of said upper and bottom holders and said absorbent collector having said crime evidence specimen thereon into two halves.

9. The device as claimed in claim 8 further comprising an identification indicia bisected by said separation line.

10. The device as claimed in claim 2 further comprising a first identification indicia on said subject information portion and a second identification indicia on said subject biological specimen collection absorbent holder portion.

11. The device as claimed in claim 10 wherein said first and second indicia are identical.

12. The device as claimed in claim 10 wherein either first or second indicia is transferred to said holder from said absorbent collector.

* * * * *